US00PP31855P2

(12) United States Plant Patent
Yencho et al.

(10) Patent No.: US PP31,855 P2
(45) Date of Patent: Jun. 9, 2020

(54) SWEETPOTATO PLANT NAMED 'NCORNSP-025SCK'

(50) Latin Name: ***Ipomoea batatas* (L.) Lam.**
Varietal Denomination: NCORNSP-025SCK

(71) Applicant: North Carolina State University, Raleigh, NC (US)

(72) Inventors: George Craig Yencho, Raleigh, NC (US); Kenneth Vincent Pecota, Raleigh, NC (US); Meri K. Reeber, Apex, NC (US); Dominic Alexander Gillooly, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/501,221

(22) Filed: Mar. 8, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen M Redden
(74) *Attorney, Agent, or Firm* — Myers Bigel, P.A.

(57) ABSTRACT

'NCORNSP-025SCK' is a moderately compact to compact, non-twining, slightly upright variety producing many short shoots. It is distinguishable from other cultivars by its lime-green palmate shaped leaves with a lobed base; a compact habit and slightly upright mounding plant architecture. Yellow-green leaves, short internodes, and plant architecture makes 'NCORNSP-025SCK' unique amongst the current ornamental sweetpotatoes in the marketplace. 'NCORNSP-025SCK' also exhibits very good vigor and is well branched.

5 Drawing Sheets

Latin name of the genus and species: The Latin name of the novel, ornamental plant variety disclosed herein is *Ipomoea batatas* (L.) Lam.

Variety fenomination: The inventive cultivar of *Ipomoea batatas* disclosed herein has been given the varietal denomination 'NCORNSP-025SCK'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by fanners worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown as a potted plant and/or in a mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-025SCK' was bred to meet the increasing demand for new ornamental sweetpotatoes. 'NCORNSP-025SCK' is a compact, non-twining, semi-upright variety producing many short shoots. It is distinguishable from other *Ipomoea batatas* cultivars by its yellow-green palmate 3-5 moderately lobed leaves, a compact habit and semi-erect mounding plant architecture. The yellow-green leaves, short internodes, and the plant architecture makes 'NCORNSP-025SCK' unique amongst the current ornamental sweetpotatoes in the marketplace. 'NCORNSP-025SCK' exhibits very good vigor and is very well branched. In greenhouse and field trials conducted since 2015 'NCORNSP-025SCK' has been shown to be much less vigorous than *Ipomoea batatas* cultivars 'Margarita' (unpatented) and 'Blackie' (unpatented) and is suitable for use as a landscape or containerized plant. Of the common cultivars of ornamental sweetpotato, 'NCORNSP-025SCK' is best compared with 'Sweet Caroline Light Green' (U.S. Plant Pat. No. 15,028) and 'NCORNSP-012EMLC' (U.S. Plant Pat. No. 21,744) cultivars. Like 'Sweet Caroline Light Green', 'NCORNSP-025SCK' has yellow-green leaves and a moderately compact habit. However, the habit of 'NCORNSP-025SCK' is more compact and erect than 'Sweet Caroline Light Green', which is slightly trailing. 'NCORNSP-012EMLC' has very deeply lobed leaves, with 5-7 lobes. 'NCORNSP-025SCK' has moderately lobed leaves, with 3-5 lobes. The production of flowers by 'NCORNSP-025SCK' is infrequent under short day conditions.

Lineage. 'NCORNSP-025SCK' (breeding designation NC8995-001ORN) originated from a conventional cross between the proprietary *Ipomoea batatas* breeding lines NCORN8555-004ORN (the female parent; not patented) and NC8524-003ORN (the male parent; not patented). Botanical seed was harvested from the NCORN8555-004ORN x NC8524-003ORN cross and other ornamental sweetpotato lines planted in our winter greenhouse-crossing block between September of 2013 and March of 2014 in Raleigh, N.C. NC8555-004ORN resulted from open pollinated seed harvested from the proprietary *Ipomoea batatas* breeding line NC8241-008ORN (the female parent; not patented). NC8524-003ORN resulted from open pollinated seed harvested from the proprietary *Ipomoea batatas* breeding line NC7840-059ORN (the female parent; not patented). Botanical seed from the NCORN8555-004ORN x NC8524-003ORN cross was planted in the greenhouse in February of 2015. The first cycle of selection on the materials derived from the NCORN8555-004ORN x NC8524-003ORN cross was exercised at the seedling tray stage and survivors were transferred to a single 6-inch pot, which was then maintained in a virus-free greenhouse. Cuttings (2 each) were taken from the plants in April and planted in the field as 2-plant unreplicated plots during mid-June 2015. The single, individual plant now known as 'NCORNSP-025SCK' was selected Aug. 31, 2015 because of its combination of exceptional features, and it has been propagated asexually as vegetative material from the original 6-in pot in the sweetpotato breeding greenhouse and via tissue culture in Raleigh, N.C. since that time since that time.

Asexual Reproduction. Since its selection, *Ipomoea batatas* 'NCORNSP-025SCK' has been asexually reproduced in North Carolina predominantly by vegetative propagation of vine cuttings. Successively, there have been six cycles of vegetative propagation, one cycle of tissue culture micropropagation, and multiple vegetative propagation cycles to increase the plant population. Asexual reproduction of 'NCORNSP-025SCK' by cuttings has shown that the unique features of the new cultivar are stable and that the plant reproduces true to type in successive generations.

SUMMARY OF THE INVENTION

'NCORNSP-025SCK' is a compact, non-twining, semi-upright variety producing many short shoots. It is distinguishable from other cultivars by its yellow-green, palmate moderately lobed leaves with 3-5 lobes; a compact habit and semi-erect mounding plant architecture. The yellow-green leaves, short internodes, and compact plant architecture are what make 'NCORNSP-025SCK' unique amongst the current ornamental sweetpotatoes in the marketplace. 'NCORNSP-025SCK' also exhibits very good vigor and is very well branched. In greenhouse and field trials conducted since 2015, 'NCORNSP-025SCK' has been shown to be much less vigorous than *Ipomoea batatas* 'Margarita' and 'Blackie' and is suitable for use as a landscape or containerized plant. The production of flowers by 'NCORNSP-025SCK' sporadic under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION OF THE NEW VARIETY

Figure 1A:
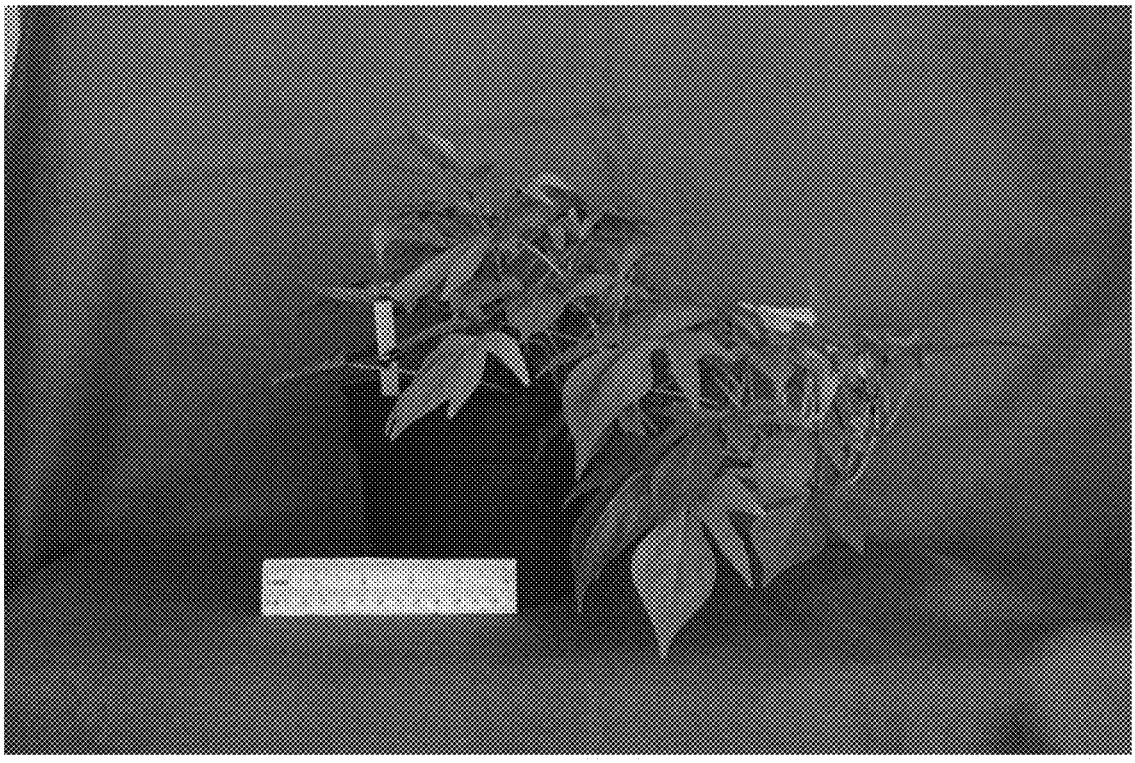
FIGS. 1A-1B is a color photograph of a typical specimen of greenhouse grown *Ipomoea batatas* 'NCORNSP-025SCK' in a 6-inch pot from the side (FIG. 1A) and top (FIG. 1B), 59 days after planting.
Figure 1B:
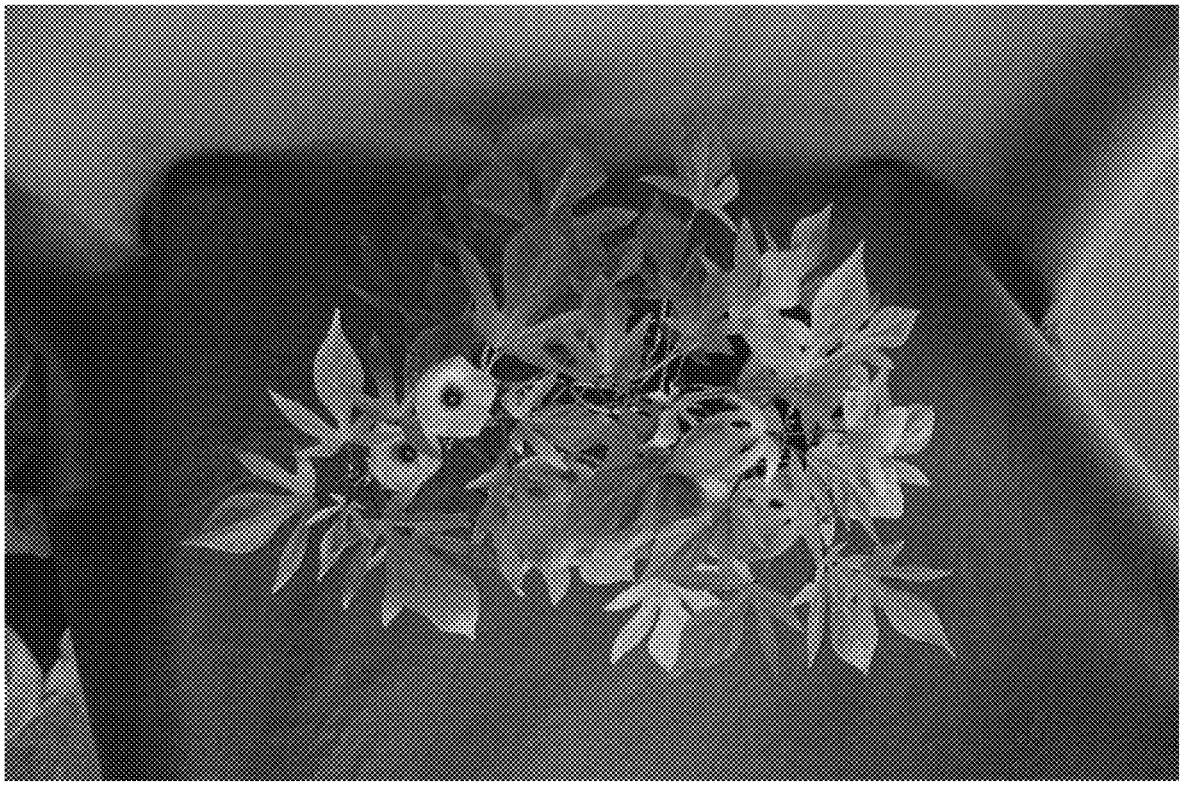
Figure 2A:
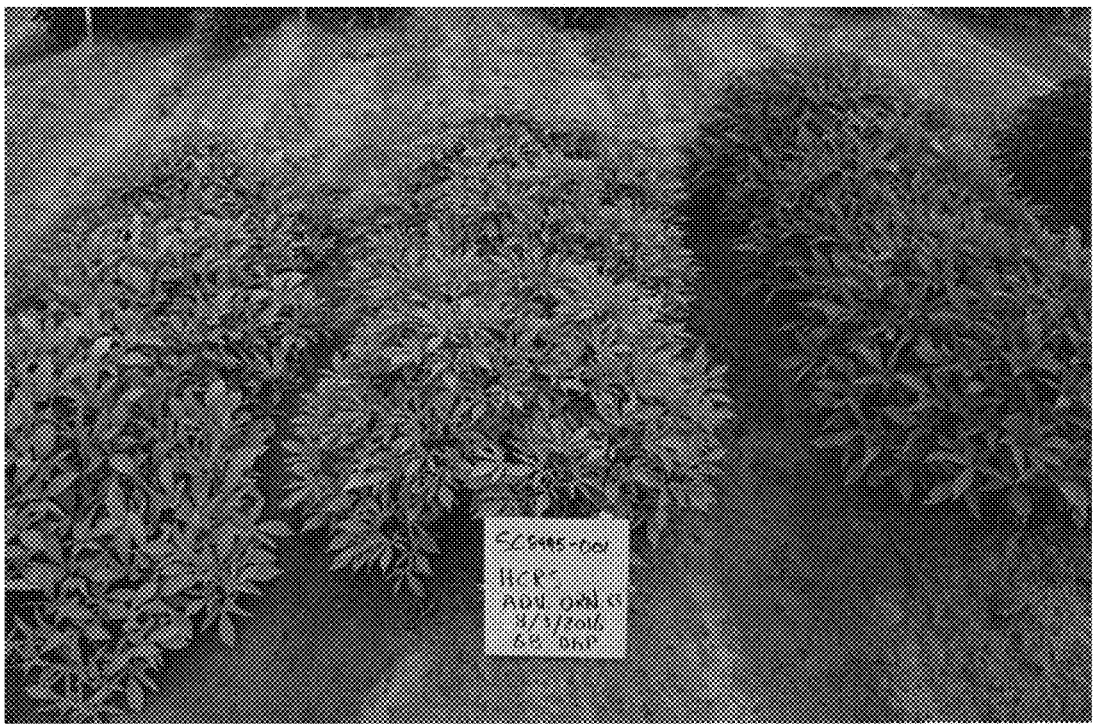
FIGS. 2A-2B is a color photograph of a typical specimen of *Ipomoea batatas* 'NCORNSP-025SCK' from side (FIG. 2A) and top (FIG. 2B) in the field, 68 days after planting.
Figure 2B:
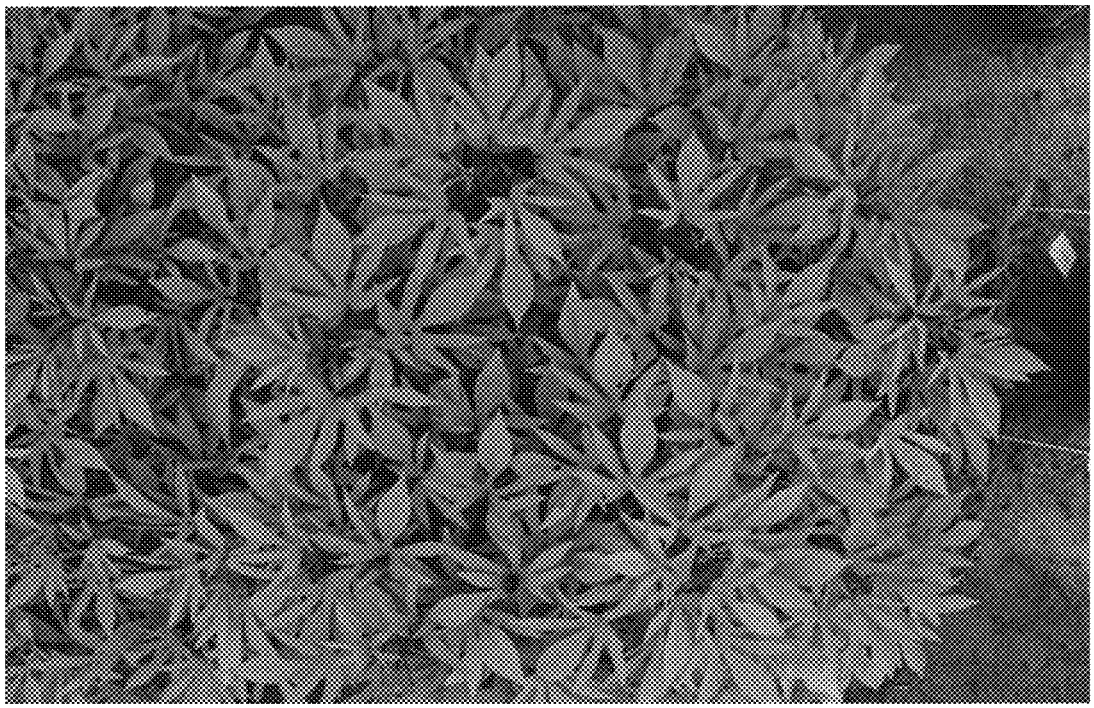
Figure 3A:
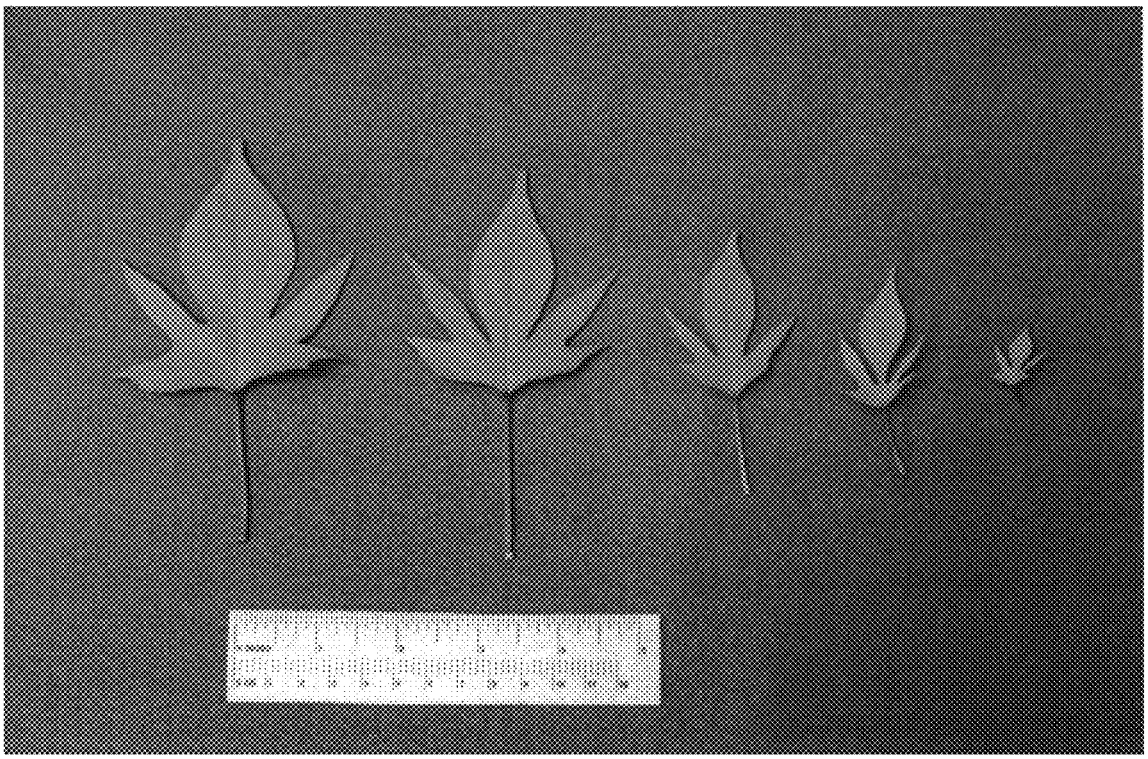
FIGS. 3A-3B is a color photograph showing the showing upper (FIG. 3A) and lower (FIG. 3B) surfaces of immature (right) to mature (left) leaves produced by *Ipomoea batatas* 'NCORNSP-025SCK'.
Figure 3B:
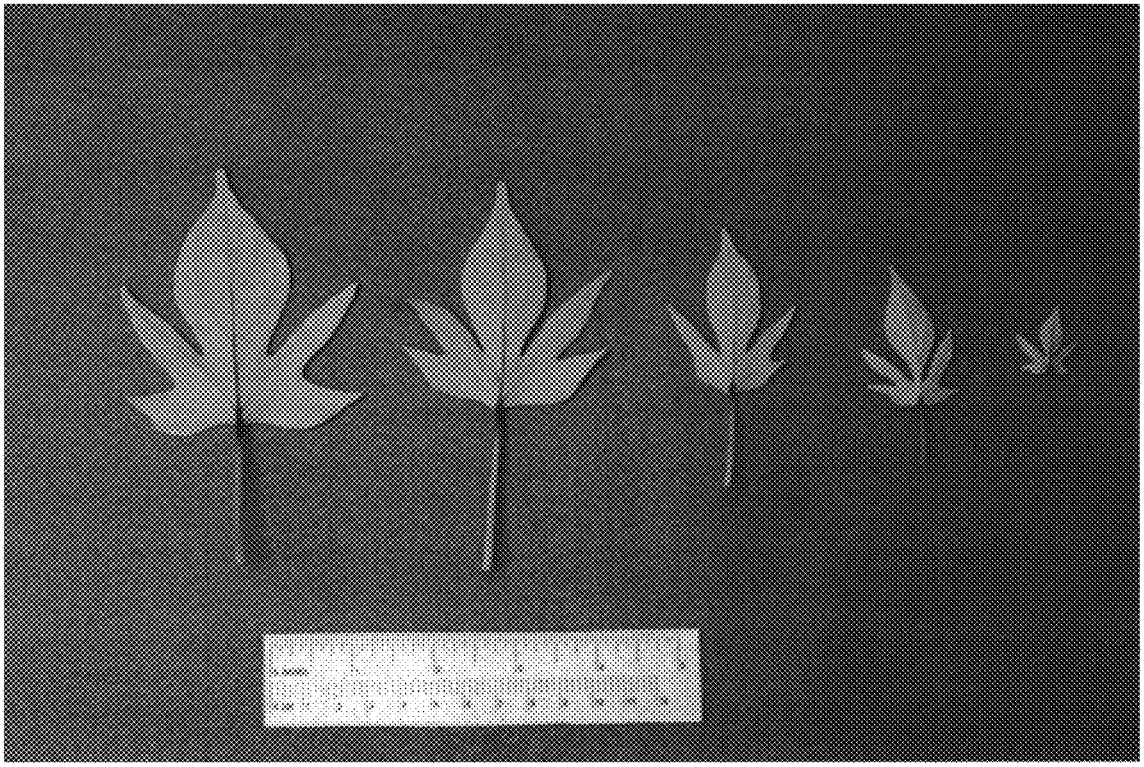

The following is a detailed description of the botanical characteristics of a new and distinct cultivar of *Ipomoea batatas* plant known by the cultivar name 'NCORNSP-025SCK'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions reported herein are from a group of 59-day-old specimens grown individually in six-inch azalea pots. The plants were grown in Raleigh, N.C., under commercial practice in a glass-covered greenhouse, where, during the fall, day and night temperatures range between 30-40° C. and 22-26° C., respectively. After rooting, plants were treated with 200 ppm 20-10-20 fertilizer weekly. Plant histories were taken in December 2017 in Raleigh, N.C. *Ipomoea batatas* 'NCORNSP-025SCK' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-025SCK'.

Growth conditions: *Ipomoea batatas* 'NCORNSP-025SCK' has very good vigor and a moderate growth rate. In locales with mild winter conditions, *Ipomoea batatas* 'NCORNSP-025SCK' will grow perennially; otherwise it is an annual plant. Similar to other cultivated sweetpotatoes, wind or rain rarely causes much damage to 'NCORNSP-025SCK', but if damage does occur, the plant drops the damaged leaves and grows new shoots at nodes where the leaves were lost. Under low light levels in a greenhouse, 'NCORNSP-025SCK' can develop intumescence, which will remain on the affected foliage, but will be outgrown with new foliage.

Aboveground structure and coloration: FIGS. 1A, 1B, 2A, 2B, 3A and 3B show the shape and coloration of a typical specimen of *Ipomoea batatas* 'NCORNSP-025SCK'. Color will vary somewhat due to temperature and nutrient stress. Overall, this cultivar is a compact, non-twining, semi-upright herbaceous plant that has an average height of ~16.2 cm and an average area spread of ~51.1 cm. The growth habit of this plant is to grow upright with shoots growing upward and outward.

Branches:

*Branching habit*.—Freely-branching with ~3-4 primary lateral branches coming off the stem. Very dense foliage and no pinching is required to stimulate branching. Branch texture is smooth and glabrous with slight pubescence.

*Vegetative lateral branching*.—Length: ~27.6 cm. Diameter: ~0.5 cm. Internodes are short with an average length of ~1.6 cm.

*Secondary lateral shoots*.—No measurable secondary lateral shoots formed on the rated plants.

*Stem*.—Round, smooth and glabrous with a slight pubescence, with an upward, very strong, slightly flexible, non-brittle strength. Color: Yellow-Green (RHS 144 A-B) and greyed-purple (RHS 187 A) at internodes and spots along stems.

*Adventitious roots*.—Present at nodes. Color: purple (RHS N79A).

*Petiole*.—Petioles are held slightly upward and curve outward. Leaf petiole has a smooth glabrous texture. Length: ~9.6 cm. Diameter: ~0.3 cm. Color: Yellow-green (RHS 144 A-B) and purple (N77C) at petiole junction purple (N77C).

Foliage: Leaves are alternate and tend to slightly spiral around the stem. They are simple and moderately dived into 3-5 lobes. Leaf shape is somewhat variable as is size (see FIGS. 3A-3B).

*Quantity*.—Heavily foliated, with ~21.5 leaves per lateral branch.

*Mature leaf length*.—~10.3 cm.

*Mature leaf width*.—~9.9 cm.

*Leaf margin*.—Entire.

*Leaf apex*.—Acuminate.

*Leaf base*.—Lobed.

*Leaf texture*.—Glabrous texture and matte finish.

*Venation*.—Arcunate to cross-venulate. Texture: Glabrous.

*Color*.—Leaves are yellow-green and range within that palate as they mature. See also Table 1.

TABLE 1

Leaf color of *Ipomoea batatas* 'NCORNSP-025SCK'.

| Leaf Structure | Upper Surface | Lower Surface |
|---|---|---|
| Young Leaf | Yellow-Green (RHS 144A-B) | Yellow-Green (RHS 147C) |
| Mature Leaf | Yellow-Green (RHS 144B-C) | Yellow-Green (RHS 147C-D) |
| Vein-mature leaf | Yellow-Green (RHS 144B-C) | Yellow-Green (RHS 147C) |
| Vein-young leaf | Yellow-Green (RHS 144B-C) | Purple (RHS N79B) |

Inflorescence: The production of flowers by 'NCORNSP-025SCK' is very sporadic under short day conditions and we have not been able to obtain flowers for the measurement of flower traits.

Figure 4:
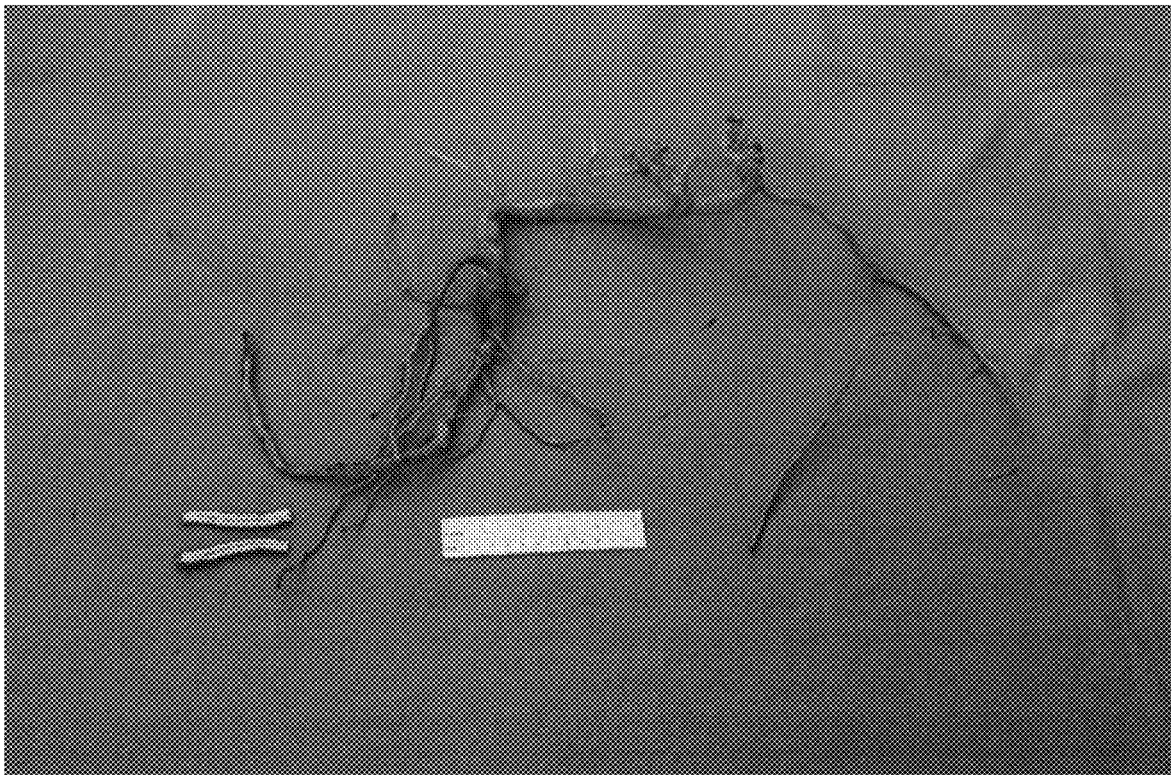
FIG. 4 is a color photograph showing the storage roots produced by *Ipomoea batatas* 'NCORNSP-025SCK' in the field, 133 days after planting.

Storage root coloration: Plants form no, to small, underground storage roots that are occasionally malformed and do not meet USDA Sweetpotato Storage Root Grade Standards (see FIG. 4). Fibrous roots are typically cream colored (RHS 155B). Storage roots that are formed possess greyed-red (RHS 178A) skin and a yellow-white flesh (RHS 158C).

Disease or pest resistance: 'NCORNSP-025SCK' is susceptible to whiteflies (*Trialeurodes vaporarium*) and thrips (order Thysanoptera) in a greenhouse environment. 'NCORNSP-025SCK' is susceptible to damage by Japanese beetles (*Popilla japonica*) under outdoor conditions. The resistance or susceptibility of 'NCORNSP-025SCK' to other known insects and pathogens of sweetpotato is unknown. Under low light conditions, slight edema may occur.

COMPARISON WITH PARENT PLANTS

'NCORNSP-025SCK' (aka NC8995-001ORN) and its maternal (NCORN8555-004ORN) and paternal (NC8524-003ORN) parents are very similar. However, the proximal leaf lobing differ in that 'NCORNSP-025SCK' has deeper lobing than both of the parents. Additionally, NCORN8555-004ORN has a slightly paler tip color and smaller leaf size than 'NCORNSP-025SCK', while NC8524-003ORN is less uniform in color compared 'NCORNSP-025SCK'.

COMPARISON WITH OTHER *IPOMOEA BATATAS* CULTIVARS

'NCORNSP-025SCK' is distinct based on leaf shape and plant architecture. Of the common cultivars of ornamental sweetpotato, 'NCORNSP-025SCK' is best compared with the cultivars 'Sweet Caroline Light Green' (U.S. Plant Pat. No. 15,028) and 'NCORNSP-012EMLC' (U.S. Plant Pat. No. 21,744) (Table 2). Like 'Sweet Caroline Light Green', 'NCORNSP-025SCK' has yellow-green leaves and a moderately compact habit. However, the habit of 'NCORNSP-025SCK' is more compact and erect than 'Sweet Caroline Light Green', which is slightly trailing. 'NCORNSP-012EMLC' has very deeply lobed leaves, with 5-7 lobes. 'NCORNSP-025SCK' has moderately lobed leaves, with 3-5 lobes.

'NCORNSP-025SCK' has a moderately compact to compact, slightly upright, non-twining plant habit compared with the moderately compact, slightly trailing habit of 'Sweet Caroline Light Green' and the compact, semi-upright, mounding habit of 'NCORNSP-012EMLC'. Furthermore, 'NCORNSP-025SCK' has a smaller average leaf size compared with the leaves of 'Sweet Caroline Light Green' or 'NCORNSP-012EMLC'.

TABLE 2

Comparison of 'NCORNSP-025SCK' with other Ipomoea batatas cultivars.

| Characteristic | 'NCORNSP-025SCK' | 'Sweet Caroline Light Green' (U.S. Plant Pat. No. 15,028) | 'NCORNSP-012EMLC' (U.S. Plant Pat. No. 21,744) |
|---|---|---|---|
| Plant Habit | Moderately compact to compact, slightly upright and mounding plant habit | Moderately compact, slightly trailing and mounding plant habit | Compact, semi-upright and mounding habit |
| Average Leaf Length and Width | Length: 10.3 cm Width: 9.9 cm | Length: 12.4 cm Width: 10.5 cm | Length: 14.0 cm Width: 15.5 cm |

TABLE 2-continued

Comparison of 'NCORNSP-025SCK' with other Ipomoea batatas cultivars.

| Characteristic | 'NCORNSP-025SCK' | 'Sweet Caroline Light Green' (U.S. Plant Pat. No. 15,028) | 'NCORNSP-012EMLC' (U.S. Plant Pat. No. 21,744) |
|---|---|---|---|
| Foliage Color | Yellow-green (RHS 144B-C) | Yellow-green (RHS 151A-B) | Yellow-green (RHS N144C) |
| Leaf Shape | Moderately lobed, 3-5 lobes. Entire with an acuminate apex and a lobed base | Moderately lobed, 3-5 lobes. Entire with an acuminate apex and acute base | Deeply lobed, 5-7 lobes. Entire with an acuminate apex and cordate base |

We claim:

1. A new and distinct cultivar of *Ipomoea batatas* plant named 'NCORNSP-025SCK', substantially as illustrated and described herein.

* * * * *